United States Patent
Qureshi et al.

(10) Patent No.: US 10,022,191 B2
(45) Date of Patent: Jul. 17, 2018

(54) OBJECT-TRACKING SYSTEMS AND METHODS

(71) Applicant: Restoration Robotics, Inc., San Jose, CA (US)

(72) Inventors: Shehrzad A. Qureshi, Palo Alto, CA (US); Kyle R. Breton, Fremont, CA (US); John A. Tenney, Piedmont, CA (US)

(73) Assignee: RESTORATION ROBOTICS, INC., San Jose, CA (US)

( * ) Notice: Subject to any disclaimer, the term of this patent is extended or adjusted under 35 U.S.C. 154(b) by 0 days.

(21) Appl. No.: 15/410,264

(22) Filed: Jan. 19, 2017

(65) Prior Publication Data

US 2017/0128137 A1    May 11, 2017

Related U.S. Application Data

(63) Continuation of application No. 15/193,594, filed on Jun. 27, 2016, now Pat. No. 9,589,368, which is a
(Continued)

(51) Int. Cl.
| | |
|---|---|
| *G06K 9/00* | (2006.01) |
| *A61B 34/10* | (2016.01) |
| *A61B 34/20* | (2016.01) |
| *A61B 34/32* | (2016.01) |
| *G06F 19/00* | (2018.01) |
| *G06T 7/73* | (2017.01) |
| *G06T 7/11* | (2017.01) |
| *G06K 9/62* | (2006.01) |
| *G06T 7/40* | (2017.01) |

(Continued)

(52) U.S. Cl.
CPC .............. *A61B 34/10* (2016.02); *A61B 34/20* (2016.02); *A61B 34/32* (2016.02); *G06F 19/321* (2013.01); *G06F 19/345* (2013.01); *G06K 9/481* (2013.01); *G06K 9/6202* (2013.01); *G06K 9/6267* (2013.01); *G06K 9/78* (2013.01); *G06T 7/11* (2017.01); *G06T 7/248* (2017.01); *G06T 7/40* (2013.01); *G06T 7/74* (2017.01); *G16H 50/20* (2018.01); *A61B 2017/00752* (2013.01); *A61B 2034/105* (2016.02); *A61B 2034/2057* (2016.02); *A61B 2034/2065* (2016.02); *G06T 2207/20021* (2013.01); *G06T 2207/30088* (2013.01); *G06T 2207/30196* (2013.01); *G06T 2207/30204* (2013.01); *G06T 2207/30242* (2013.01)

(58) Field of Classification Search
None
See application file for complete search history.

(56) References Cited

U.S. PATENT DOCUMENTS

| 2001/0017936 | A1* | 8/2001 | Loussouarn | ........ G06F 19/3437 382/128 |
| 2002/0197633 | A1* | 12/2002 | Jones | ................... C12Q 1/6883 435/6.13 |

(Continued)

*Primary Examiner* — Hadi Akhavannik

(57) ABSTRACT

Systems and methods for tracking, identifying, labeling and/or classifying objects or features of interest, such as follicular units are provided. In some embodiments the identified and labeled features of interest, such as follicular units, may be used for planning hair harvesting, hair implantation and/or performing hair transplantation procedures.

20 Claims, 12 Drawing Sheets

Related U.S. Application Data continuation of application No. 14/459,968, filed on Aug. 14, 2014, now Pat. No. 9,405,971, which is a continuation of application No. 12/240,724, filed on Sep. 29, 2008, now Pat. No. 8,848,974.

(51) Int. Cl.
*G06K 9/78* (2006.01)
*G06T 7/246* (2017.01)
*G06K 9/48* (2006.01)
*G16H 50/20* (2018.01)
*A61B 17/00* (2006.01)

(56) References Cited

U.S. PATENT DOCUMENTS

| | | | |
|---|---|---|---|
| 2003/0023412 A1* | 1/2003 | Rappaport | H04W 16/20 703/1 |
| 2004/0223165 A1* | 11/2004 | Kurokawa | G01B 11/0633 356/630 |
| 2005/0021282 A1* | 1/2005 | Sammut | F41G 1/38 702/150 |
| 2007/0078466 A1* | 4/2007 | Bodduluri | A61B 17/32053 606/133 |

\* cited by examiner

OBJECT-TRACKING SYSTEMS AND METHODS

RELATED APPLICATIONS

This application is a continuation of co-pending U.S. patent application Ser. No. 15/193,594 entitled "Object Tracking Systems and Methods", filed Jun. 27, 2016, which is a continuation of U.S. patent application Ser. No. 14/459,968 entitled "Object Tracking Systems and Methods", filed Aug. 14, 2014, now U.S. Pat. No. 9,405,971, which is a continuation of U.S. patent application Ser. No. 12/240,724, entitled "Object Tracking Systems and Methods", filed Sep. 29, 2008, now U.S. Pat. No. 8,848,974.

FIELD

Embodiments disclosed herein relate generally to an object-tracking system, and more particularly, to a system and method for accurately tracking hair follicles or other sites and features on a body surface.

BACKGROUND

A hair transplantation procedure typically involves harvesting donor hair grafts from a donor area, for example, the side and back fringe areas, of a patient's scalp, and implanting them in a bald area, or recipient area. In the past, the harvested grafts were relatively large, between 3-5 mm. However, recent donor grafts may be as small as single follicular units. Follicular units (FUs) are naturally-occurring aggregates of one to five closely-spaced hair follicles that are distributed randomly over the surface of the scalp.

The follicular units may be classified, or "typed," based on the number of hairs in the unit, and identified in shorthand as an "F1" (single hair follicular unit), "F2" (two-hair follicular unit), etc. In some cases of multiple hair follicular units, the hairs may appear to emanate from a single follicle or point in the skin. In other cases, the hairs may exit the skin slightly spaced from one another.

During a hair transplant procedure, certain locations should be avoided for harvesting or implanting hairs. For example, if a doctor already used a site for harvesting or implanting hairs, the doctor may want to avoid using the same site for a subsequent procedure. Tracking devices have a difficult time tracking some of these sites.

A system is needed that may include a database of harvested and implanted sites. A doctor may use the database to plan future harvesting and implantation. The system may track and record site information even when the actual site cannot be seen, because the system can track features around the site, including follicular units, scalp features, or external markers.

A system is also needed that can track moving features. One way of tracking features is detecting their locations on a still by still basis. A system is needed that can improve tracking and does not need to detect feature locations on a still by still basis. Such a system may utilize motion vectors of features or markers to improve tracking.

SUMMARY

Briefly, and in general terms, there is disclosed an object-tracking system. More particularly, there is disclosed an object tracking system and method that track objects on a body surface that are not otherwise easily tracked.

In one aspect, a method for tracking a feature of interest, such as follicular unit, involves identifying at least one marker in a first image, the first image including the feature of interest, such as a follicular unit; computing a signature of the feature of interest in the first image; identifying the at least one marker in a second image; computing a motion vector corresponding to a change in position of the at least one marker from the first image to the second image; and using the motion vector and the signature of the feature of interest in the first image to label the feature of interest in the second image.

In another aspect, there are at least three markers in the first image. Using three or more markers allows tracking both translational and rotational movement. The at least one marker can embody one or more of another follicular unit, a mole, a scar, a freckle, a wrinkle, a bump, or a depression of the body surface. Additionally, a plurality of markers can be included in the first image and identifying the at least one marker in a first image can involve identifying a point cloud.

In one approach, a centroid of the point cloud is calculated. Computing a signature of the follicular unit in a first image can involve identifying one or more of a length, type, caliber, emergence angle, area, shape, and color of the follicular unit. Further, in one specific approach, at least one marker in the first image is labelled, and the at least one marker is labelled in the second image with the same label as in the first image by searching for the at least one marker in the second image in the direction pointed to by the motion vector.

In one embodiment, additional motion vectors could be used. For example, a second motion vector is computed from the first image and the second image, and the second motion vector is used to label the follicular unit in the second image. The second vector can be computed using one or more of the Gray-Coded Bit-Plane, optical flow, and block search image stabilization techniques.

In various other aspects, an image-capture device is moved according to the motion vector to keep the feature of interest, such as follicular unit, in a field of view of the image-capture device. Moreover, identifying the at least one marker can involve associating electronic identifiers with the at least one marker. Also, any marker in the second image inconsistent with its location in the first image according to the motion vector is discarded from consideration.

Additionally, the motion vector can define a search region for locating the follicular unit or other feature of interest. Defining the search region involves analyzing a region along the motion vector and within a predetermined distance from the motion vector. The predetermined distance from the motion vector can embody a cone having a tip at a location of the marker in the first image, the tip having a predetermined tip angle, the cone extending in a direction of the motion vector and including an area within the predetermined tip angle.

In various specific approaches, the first and second images are divided into a plurality of first and second sub-images, and a plurality of motion vectors from the first and second sub-images are computed. Further, the follicular unit that has been tracked may be harvested from a donor area and may be implanted in a recipient area.

In another aspect, a method for tracking a feature of interest, such as a follicular unit, can involve receiving a first image of a body surface containing follicular units and a second image of the same body surface; identifying a follicular unit in the first image; computing a signature of the follicular unit in the first image; computing a motion vector from the first image and the second image; and using the motion vector and the signature of the follicular unit in the first image to label the follicular unit in the second image. The motion vector could be computed without using any markers but rather from the image as a whole. Computing the signature of the follicular unit in the first image can include identifying one or more of a length, type, caliber, emergence angle, area, shape, and color of the follicular unit.

In yet another aspect, a system for tracking a feature of interest, such as a follicular unit, on a body surface includes an imaging device for capturing at least two images, a first image including a first marker and a follicular unit; a signature identification component, wherein the signature identification component identifies signature information about the follicular unit; a vectoring component, wherein the vectoring component calculates a motion vector between a first image of the two images and a second image of the two images; and a tracking system for receiving data corresponding to the motion vector, and labelling the follicular unit based on the motion vector and the follicular unit signature information. The tracking system can be further programmed to move the imaging device based on the motion vector. The signature identification component, vectoring component, and tracking system can be part of a single computer-program product. Moreover, the system for tracking a follicular unit or other feature of interest on a body surface can further embody a marker identification component. The marker identification component may be a part of the signature identification component or may be a separate component or program. Also, one or more of the signature identification component, the vectoring component, and the tracking component can include a processor connected to at least one of memory and the imaging device.

The imaging device can be a camera, and the system may be a robotic system further including a robotic arm. Also, the imaging device can be operably connected to the robotic arm. It is also contemplated that a system for tracking/labelling feature of interest, such as follicular units, may include an interface adapted to receive an image data containing follicular units; and an image processor comprising one or more modules for executing operations on the image data, the one or more modules including instructions for: receiving a first image of a body surface containing follicular units and a second image of the same body surface; identifying a follicular unit in the first image; computing a signature of the follicular unit in the first image; computing a motion vector from the first image and the second image; and using the motion vector and the signature of the follicular unit in the first image to label the follicular unit in the second image.

In another aspect, a computer program tangibly embodied in a computer-readable memory medium and including instructions that cause a processor of a computing device to execute a computer process for tracking a feature of interest, such as a follicular unit, comprises identifying at least one marker in a first image, the first image including a follicular unit; computing a signature of the follicular unit in the first image; identifying the at least one marker in a second image; computing a motion vector corresponding to a change in position of the at least one marker from the first image to the second image; and using the motion vector and the signature of the follicular unit in a first image to label the follicular unit in the second image. Further, it is contemplated that the processor is operatively associated with the memory. The computer process can also involve comparing first marker data from the first image to first marker data from the second image and storing a resulting vector in memory. The computer program can be operatively associated with an image-capture device.

In still other aspects, a method for tracking a feature of interest (for example, a follicular unit) on a body surface involves identifying at least one marker in a first still image, the first still image containing a feature of interest; computing a signature of the feature of interest in the first image; defining a frame of reference corresponding to the at least one marker; locating the at least one marker in a second still image; and detecting a position of the feature of interest in the second still image using the computed signature and updating a translational component of the frame of reference based on a position of the at least one marker in the second still image.

An approach can also include identifying at least three markers in a first still image, and wherein detecting a position of the feature of interest in the second still image comprises updating both translational and rotational components of the frame of reference. Further, the at least one marker in the first still image could be identified by, for example, analyzing at least one of a length, an area, a shape, a type, or a color of such marker.

Additionally, the at least one marker can be a follicular unit and identifying the at least one marker further comprises analyzing at least one of the emergence angle of the follicular unit from the body surface and the caliber of the hair. The still images can be video images of a body surface, the at least one marker is a follicular unit on the body surface, and the feature of interest is another follicular unit on the body surface.

The frame of reference can be updated by using a point cloud approach and an imaging device can be moved according to an average shift of the point cloud. A feature of interest can be a bald spot and the method can further involve defining one or more hair implantation sites.

In another approach, a method for tracking a features of interest (such as a follicular unit) on a body surface includes identifying at least three markers in a first still image, the first still image displaying a feature of interest; computing a signature of the feature of interest in the first still image; tracking at least three first objects in the first still image; defining a frame of reference corresponding to the three markers; determining whether the three markers are in a second still image; and in response to at least one of the three markers not being in the second still image, detecting a position of the feature of interest in the second still image using the computed signature of the feature of interest and updating the frame of reference based on a position of any of the at least three markers in the second still image and any of the first objects in the second image. A sum of a combination of markers and first objects used to detect the position of the feature of interest is at least three.

At least one of the at least three first objects can include a follicular unit, a mole, a scar, a freckle, a wrinkle, a bump, or a depression of the body surface. Detecting the position of the feature of interest can further involve computing a motion vector from the first still image and the second still image and using the motion vector to update the frame of reference and to locate at least one of the at least three markers. At least one first object in the first still image is identified and the identified first object is located in the second still image, and computing the motion vector includes identifying a change in position of the identified first object from the first image to the second image.

It is also contemplated that a system for tracking a feature of interest on a body surface can include an interface adapted to receive a plurality of images from an image capture device, at least a first image comprising a feature of interest; a signature identification component, wherein the signature identification component identifies signature information about the feature of interest and detects at least one marker in the first image; and a marker referencing system. The referencing system defines a frame of reference corresponding to the at least one marker, determines whether the at least one marker is in a second image, and adjusts the frame of reference corresponding to a change in position of the at least one marker from the first image to the second image to locate the feature of interest. The signature identification component and the marker referencing system can be part of a single computer program product. Also, the signature identification component can include a processor connected to memory, and the processor associates an electronic identifier with the at least one marker and stores the electronic identifier in the memory. Moreover, the marker referencing system can include a processor connected to memory, and the processor compares a location of each of the at least one marker in the first image to a location of each of the at least one marker in a second image, calculates a corresponding change in a frame of reference, and stores a result of the calculation in the memory. The system may further comprise a vectoring component. The system can be a robotic system further including a robotic arm.

Other features and advantages will become apparent from the following detailed description, taken in conjunction with the accompanying drawings, which illustrate by way of example, the features of the various embodiments.

BRIEF DESCRIPTION OF THE DRAWINGS

The invention is illustrated by way of example and not limitation in the figures of the accompanying drawings. In the drawings, identical reference numbers identify similar elements or acts. The sizes and relative positions of elements in the drawings are not necessarily drawn to scale. For example, the shapes of various elements and angles are not drawn to scale, and some of these elements are arbitrarily enlarged and positioned to improve drawing legibility. Further, the particular shapes of the elements as drawn, are not intended to convey any information regarding the actual shape of the particular elements, and have been solely selected for ease of recognition in the drawings.

DETAILED DESCRIPTION

Figure 1:
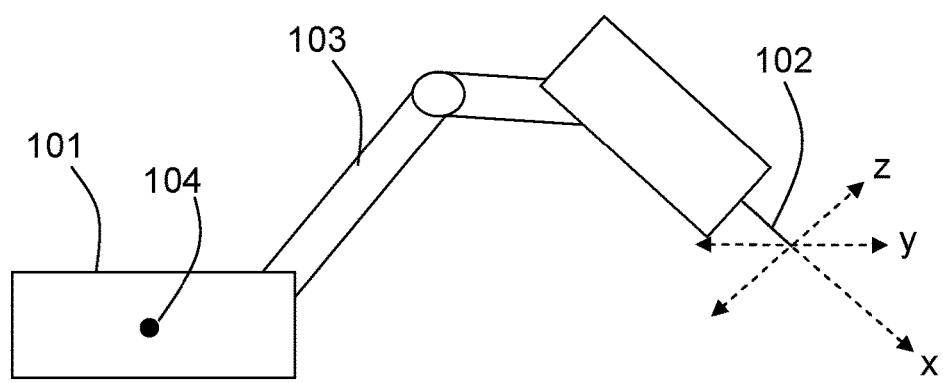
FIG. 1 illustrates a kinematic "frame"

The various embodiments described below are provided by way of illustration only and should not be construed to limit the claimed invention. Those skilled in the art will readily recognize various modifications and changes that may be made to the disclosed embodiments without departing from the scope of the claimed invention. By way of non-limiting example, it will be appreciated by those skilled in the art that particular features or characteristics described in reference to one figure or embodiment may be combined as suitable with features or characteristics described in another figure or embodiment. Further, those skilled in the art will recognize that the devices, systems, and methods disclosed herein are not limited to one field, such as hair restoration, but may be applied to any number of fields that require objects to be tracked.

The described systems and methods of the present disclosure are useful in any application that requires tracking of individual objects via image guidance. They are also useful in any application where it is desired to register a set of visual markers to create a reference frame and then track an object by using surrounding objects to update the reference frame, rather than tracking the object directly. For example, the concept of using the output of image stabilization algorithms to guide or steer an object tracker could find its way into a wide range of medical and non-medical application, such as image guided robotic procedures involving fluoroscopy or x-ray imaging where fiducials are inserted into the anatomy, or video surveillance applications that include pan-tilt-zoom cameras in conjunction with analytics to track moving objects through a dynamically changing scene.

The systems and methods of the present disclosure are especially useful in hair transplantation procedures, including automated or computer-controlled hair harvesting and implantation. Therefore, various examples and embodiments described herein will use follicular units or hairs simply as one example of the application of the present disclosure for purposes of describing some embodiments with the understanding that it represents more broadly all other appropriate applications.

It should be understood that the exemplary methods described herein are especially suited for use with a robotic system for treatment planning, hair harvesting and/or implanting. However, they are not limited by any means to the robotic applications; instead the described methods may be applied to the manual procedures conducted by a human with a hand-held device that could be, for example, operably connected to the computer processor and imaging system. Manual, partially-, and fully-automated systems are also within the scope of the present invention.

When performing medical operations on a patient's skin or scalp, certain areas need to be tracked, so that a doctor or, for example, a robotic mechanism in case of the automated procedures, may return to the area, or avoid the area, at a later time. These areas may be tracked by viewing images of the area and identifying features on or around the area. The identifying features are registered by recording data about the features in a database, memory, or other data storage medium. The identifying features may be accessed at a later time and compared with still images, or "stills," to determine whether a region shown in the still is the same as the region containing the identifiers. "Stills" may be single images of a video feed, photographs, or other fixed representations of the patient's skin.

One method of registering an area or feature involves identifying a set of markers in a specific pattern in a still that could be recognized in the future. The markers are non-collinear, so they define a 3-D frame. Although a minimum of three markers are desirable to define a 3-D frame, more markers may be used. These markers in the still are called a "registration pattern" and can be recognized in subsequent stills. The 3-D frame, consisting of coordinates x, y, z, and rotation coordinates Rx, Ry, and Rz, is called a "patient frame." In each successive still where the registration pattern is completely visible and identifiable, the patient frame is simply moved with the updated registration pattern. Coordinates x, y, and z may be referred to as the translation of the patient frame. Coordinates Rx, Ry, and Rz may be referred to as the orientation of the patient frame. For clarity, the term "frame" is defined in this specification as a location and an orientation defined from a known point of reference. A single section of a video or photo is referred to in this specification as a "still" or an image. Although a still may be referred to as a "frame," this specification only uses the word "frame" as defined above in its kinematic sense, and the word "still" to describe a single image of a video feed, to avoid confusion.

FIG. 1 illustrates an example of a kinematic frame. In this exemplary embodiment, a robotic arm 103 is attached to a fixed base 101 having a center 104. The arm 103 holds and positions a tool 102. The tool has a frame, labelled x, y, z, and the location and rotation of the tool 102 is known with respect to the center 104 of the base. This location and orientation may be stored electronically. If the relationship between the tool and the center 104 of the base changes, the frame may be updated electronically.

Figure 2:
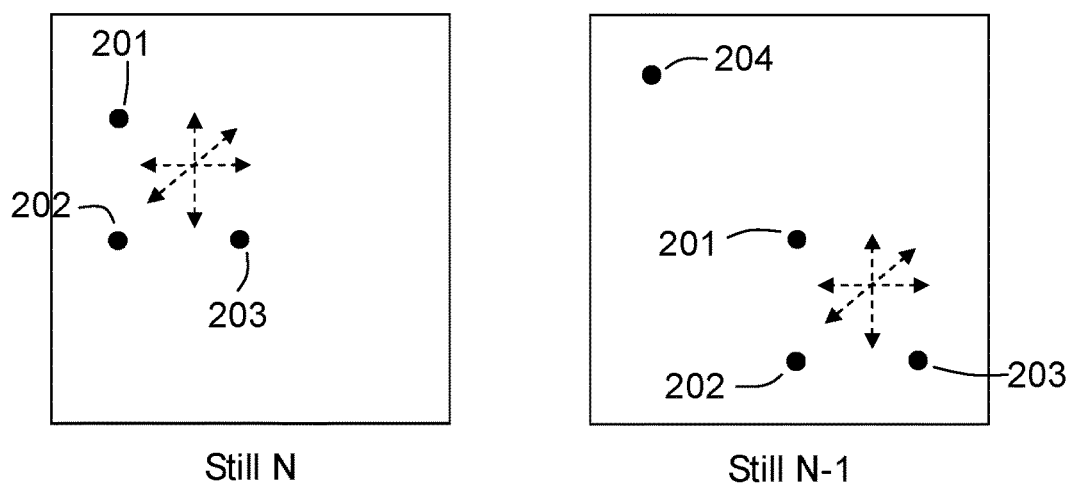
FIG. 2 illustrates updating a frame.

After the registration pattern is identified and electronically saved, the location and orientation of the frame may be updated by analyzing the position of the markers in a subsequent still. FIG. 2 illustrates updating a frame based on a change in position of markers. In a first still, still N, a three-dimensional frame is defined by the location of markers 201, 202, and 203. The markers (also called "fiducials") may be, for example, physical markers or anatomical landmarks on a patient's skin or body surface, such as a follicular unit or hair, a mole, a scar, a freckle, a wrinkle, a bump, or a depression of the body surface. The markers may also be objects placed on or affixed to the patient's skin, sometimes called external fiducials. A fiducial is an object in a field of view of an imaging device that acts as a reference. It could be anatomical landmark, an external marker, or any combination of the above. In still N-1, the markers have moved down and to the right in the still. Another object, 204, has appeared in a location similar to the marker 201 in still N. However, the object 204 would not be confused with marker 201, because the marker 201 is identified with respect to markers 202 and 203. The frame is updated in a database or memory to recognize that the patient has moved, and that object 204 is not marker 201.

Figure 3:
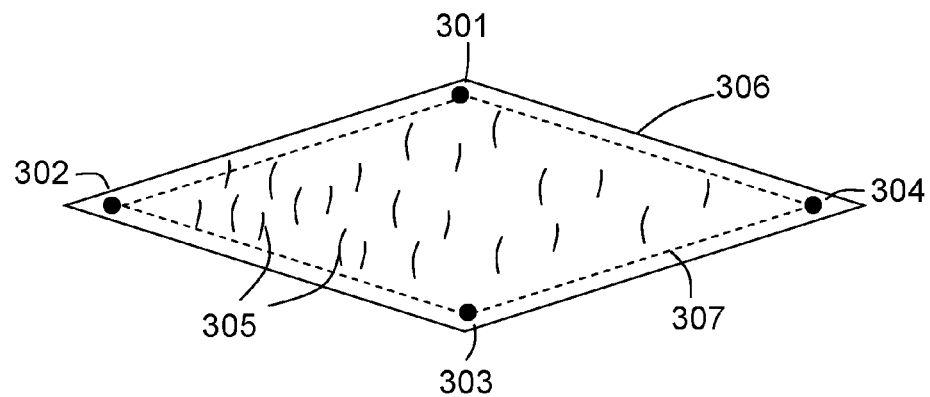
FIG. 3 illustrates harvesting planning using registration markers.
Figure 4:
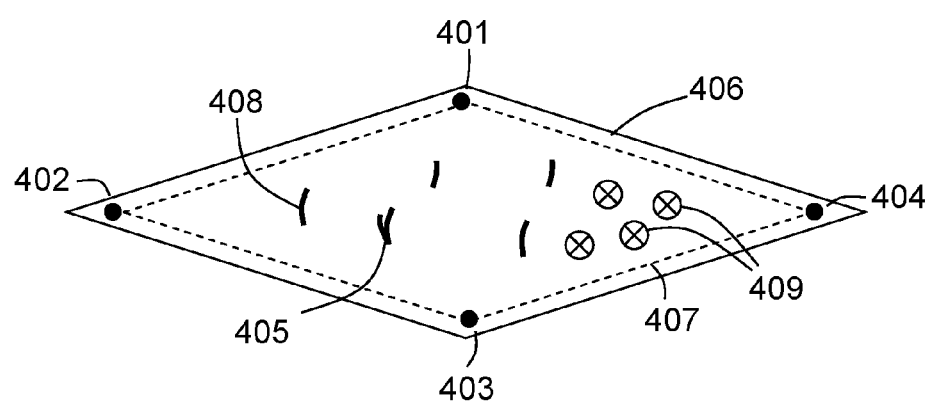
FIG. 4 illustrates implantation planning using registration markers.

In some exemplary applications, the registration pattern may be used for real-time hair harvesting and implantation planning, as shown in FIGS. 3 and 4, respectively. In FIG. 3, markers 301, 302, 303, and 304 define a patient frame. The location of each follicular unit 305 on a patient's skin 306 may be mapped with respect to the patient frame. The portion of the patient's body surface that is used to harvest follicular units is the "donor area" 307. The donor area's follicular unit density may be calculated by counting the follicular units in the still. The counting of the follicular units may be accomplished, for example, as described in the commonly assigned patent publication WO 2008/024955 which is incorporated herein by reference. A physician may determine how many follicular units per $cm^2$ to extract from the donor area and to input such information into the harvesting planning system. The harvesting planning system in turn determines which follicles to extract based on the number of follicular units and the number of desired follicular units per $cm^2$ to be extracted. Other factors may also be used to determine which follicular units to extract, including follicular unit characteristics and scalp/body surface characteristics.

Likewise, a similar methodology may be used during hair implantation. FIG. 4 illustrates an exemplary implantation method. The registration pattern comprises, for example, markers 401, 402, 403, and 404. The markers define the recipient area 407, for example, on the scalp 406. A planning system receives inputs indicating the number of follicular units to implant, and the implantation locations 409. Exemplary follicular units 408 and 405 may be analyzed to determine a follicular unit density, baldness pattern, or other criteria for implanting follicular units. The bald area on the body surface may be a feature of interest that could be tracked and labelled to create implantation sites according to the present disclosure.

A patient may move during a scalp analysis, harvesting, or implantation. The monitoring system can track each follicular unit and other areas of the scalp by comparing a still with a previous still, and updating the patient's frame to correspond with the changed position of the markers from one still to the next.

Figure 5:
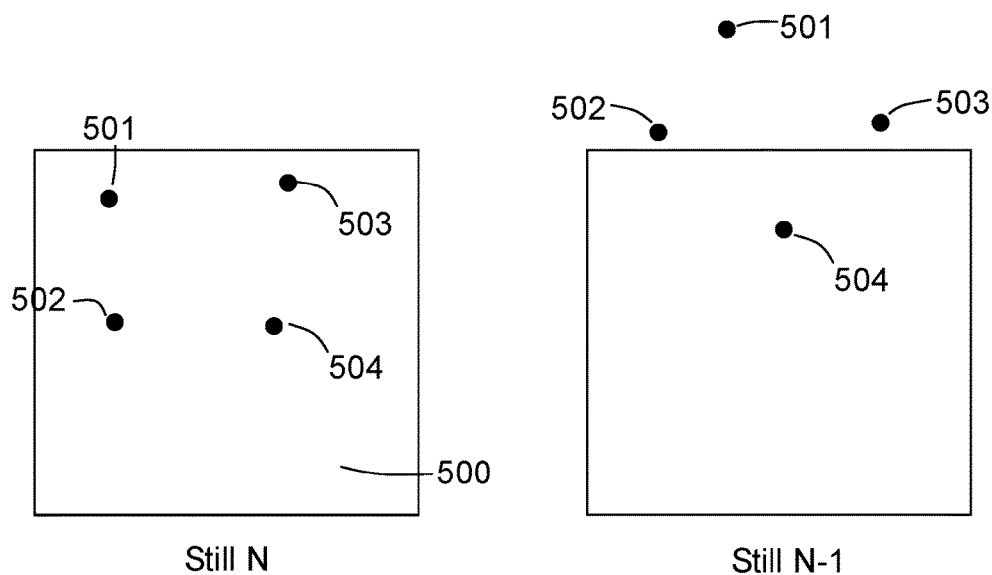
FIG. 5 illustrates updating a frame after losing a registration pattern.

However, sometimes one or more markers will not appear in a subsequent still, because the patient has moved or turned so that the markers are outside the still. Also, objects or blood may obscure or block one or more markers. FIG. 5 illustrates a patient's moving the markers out of the still. Markers 501, 502, and 503 define a patient's frame on body surface 500. In still N, all markers 501, 502, and 503 are visible. An additional marker 504 is also visible and identified, and its position may be recorded with respect to the patient's frame formed from markers 501, 502 and 503. Still N-1 shows how a patient has moved up and rotated clockwise with respect to the still. Consequently, only marker 504 is visible in still N-1. Since the location of marker 504 is known with respect to the patient frame, the patient frame may be updated corresponding to the change in position of marker 504. However, in this example marker 504 can only be used to update coordinates x, y, and z. Marker 504, alone, provides no data for updating coordinates Rx, Ry, and Rz, corresponding to the rotation of the patient's frame around each of the axes x, y, and z. Thus, marker 504 updates the translation of the patient frame but not the orientation of the patient frame.

Figure 6:
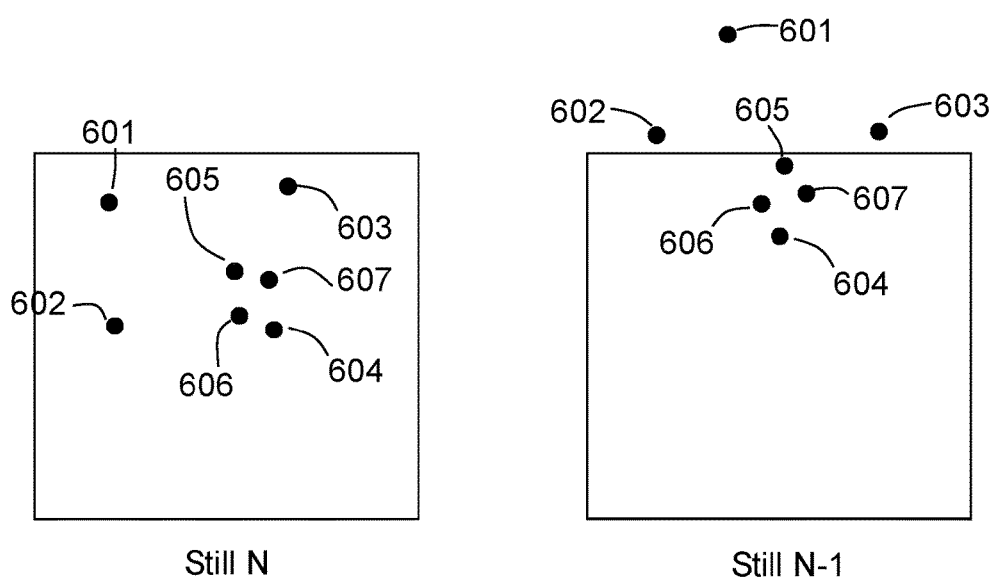
FIG. 6 illustrates updating a frame with points other than the original registration markers.

At least three non-collinear points should be visible in both still N and still N-1 in order to update both the translation and orientation of a patient frame. FIG. 6 shows a patient frame having three markers 601, 602, and 603 that define the patient frame, and four additional markers 604, 605, 606, and 607 that are identified by the system. In still N, all seven markers 601-607 are visible. In still N-1, the patient moved and rotated, and markers 601, 602, and 603 are no longer visible in the still. However, the system can use, for example, markers 604-606 that continue to stay in the field-of-view (FOV) after the patient's movement to update the patient's frame, including the orientation of the frame. As markers 604-606 are assumed to be fixed in the patient's frame, the frame may be moved such that those markers will have the same patient frame coordinates in each still.

Although external fiducials or markers may be used to define a patient frame, natural occurrences on the body surface may also be used. One of the most common features or objects on a body surface is a follicular unit comprising a certain number of hairs. Hairs are uniquely suited as markers in those applications involving hair transplantation, because the hairs are already tracked by the system for purposes of analysis, harvesting, and implantation. A center-of-mass, or centroid, of each follicular unit may be used as a marker. The movement of each centroid is tracked between stills, and the movement of one or more follicular units may be analyzed to update a patient frame. For example, if follicular units all move left by 1 mm, one may deduce that the patient frame has moved left by 1 mm. This principle works in all six degrees of freedom even if all registration markers defining a patient frame are lost from still to still, provided at least three follicular units are still visible in the FOV, as shown in the following example.

Figure 7:
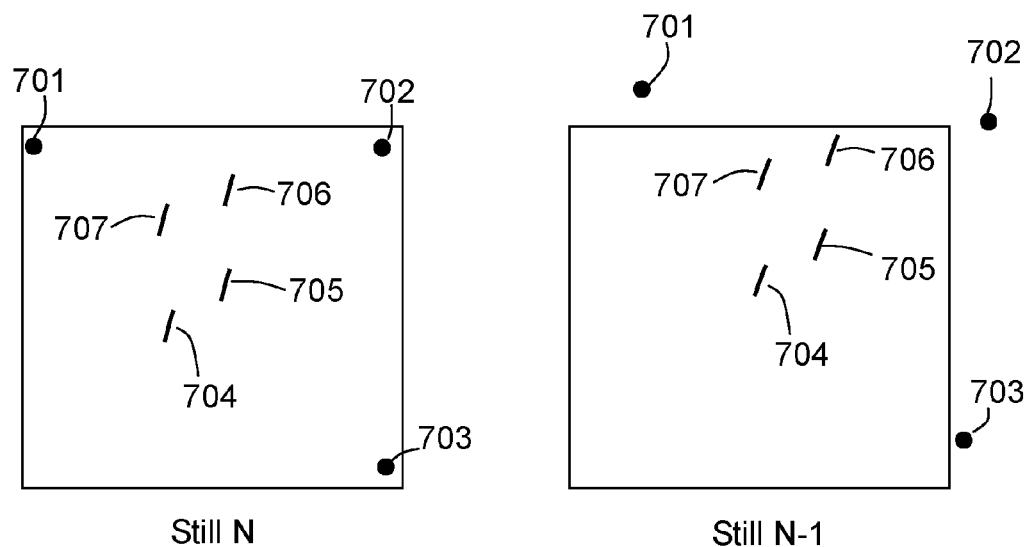
FIG. 7 illustrates updating a frame using follicular units on a patient's scalp.

FIG. 7 illustrates updating a patient frame with follicular units. In still N, markers 701, 702, and 703 are used to define a patient frame. Follicular units 704, 705, 706, and 707 are tracked for analysis, harvesting, and implantation purposes. Still N−1 shows markers 701-703 outside the still, which may occur, for example, when the body surface rotates. Since the locations of 704-707 are known with respect to the patient frame, any three follicular units of 704-707 may be used to update the patient frame, including translation and orientation.

When hairs or other registration markers are used to define or update a patient frame, the hairs may be tracked by any method, including using a point cloud algorithm. B. K. P. Horn, "Closed Form solution of Absolute Orientation Using Unit Quaturnians," J. Opt. Soc. AMA/Vol. 4 Apr. 1987, which is hereby incorporated by reference, discloses one such algorithm ("Horn algorithm").

Point cloud algorithms that estimate a rigid-body transformation between two point clouds only work robustly if the same set of points is used in both stills. A rigid-body transformation is one that preserves the shape of objects it acts on. Used in this context, a point-cloud undergoing a rigid-body transformation will have its shape preserved. Therefore, a circular-looking point cloud remains circular, a hexagonal looking point cloud remains hexagonal, etc. When using a point cloud algorithm with a body surface having many hairs, the algorithm will be most accurate if the same follicular units are used in each point cloud, and if more follicular units are used to generate the cloud. It is also important that the same follicular units comprise the point cloud in each still.

Figure 8:
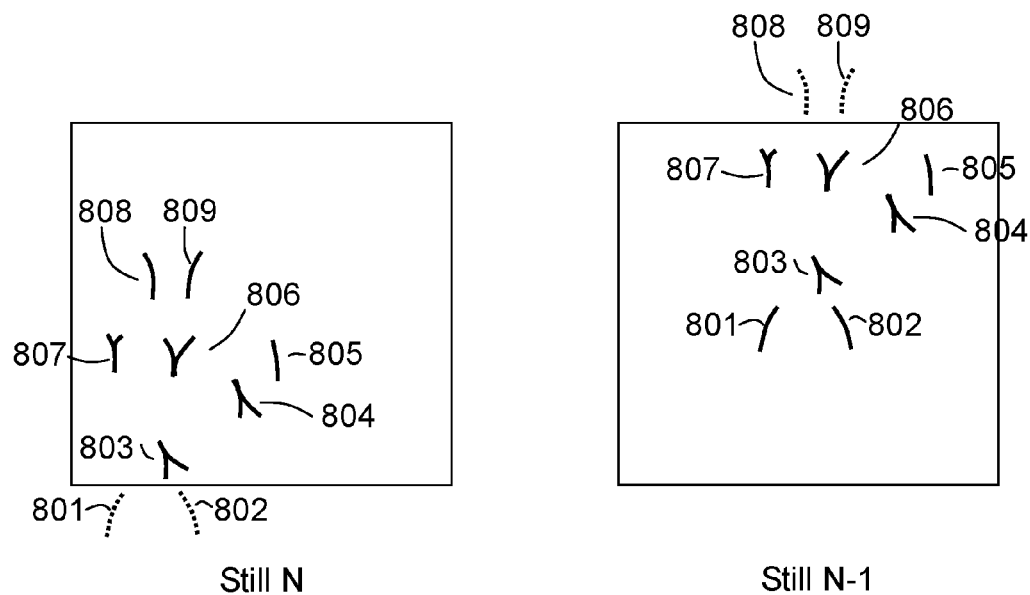
FIG. 8 illustrates a follicular unit cloud algorithm.

FIG. 8 illustrates a problem associated with the typical "Horn algorithm" that may arise when the patient moves and proper correspondence of points is not maintained from still to still. In still N, follicular units 803-809 may be used to generate a point cloud. However, in still N−1, the patient has moved, and follicular units 808 and 809 are no longer visible in the still. Also, follicular units 801 and 802 have entered the still. Since the same number of follicular units exists in each still, a system may mistakenly generate a point cloud using the seven follicular units in still N and associate it with the seven follicular units in still N−1. Since the follicular units in each still are different, the patient frame would be incorrectly updated.

To avoid the above problem, the system according to the present disclosure analyzes characteristics of the follicular units (or other appropriate features) to determine if the same follicular units exist in each still. Only the follicular units that exist in both stills are used to generate a point cloud for defining and updating a patient frame to track objects and locations on the body surface. Characteristics that may be used to identify follicular units, hairs, or other features include but are not limited to type, caliber, length, emergence angle, area, shape, color, and/or any combination of the above which would define the unique "signature" of such follicular unit or other feature used. Any other detectable characteristics or "tags" may be used to identify the follicular unit, hair, or feature.

The above-described "point cloud"-based updating of the patient frame is especially useful in implantation automation and planning for use in the robotic hair implantation system. The number of follicular units for implanting (N) is input into the system. The image processor locates any bald spots based on the images of a particular body surface using a clustering algorithm, and then generates N implant sites located within the identified bald spots. The patient frame may be formed from the surrounding hairs and possibly any viewable external markers, and each implant site is defined with respect to the patient frame. As the implanting tool (located on the robotic arm in the robotic systems, or operated by the human) moves from one site to another implanting at each defined location, the image processor may update the position of the next implant site in the set based on the updated patient frame.

When no hairs are visible on a body surface, or the visible hairs are ineffective for identification and tracking by the system, for example, when the patient is bald or has a body surface which is extremely sparse, consisting mostly of miniaturized or "wispy" hair, features of the body surface may be used to track movement instead of hairs or follicular units. In these situations, the system and method according to the present disclosure uses the body surface, such as human scalp, which is "trackable", since it is not uniform and it contains information. For example, according to one embodiment of the method described herein, the system may compare a series of pixels or regions-of-interest (ROI) between one still (still N) and the next (still N−1). Each set of stills shows a translation movement of the body surface, and many sets of stills may be aggregated to show a single shift of the scalp, or other relevant body portion. Furthermore, in other embodiments, moles, texturing, blood, and other features and objects may be used in the comparison and to update the patient frame on a still to still basis. Any readily identifiable object or feature can be used as a surrogate marker, and then its tracked position may be used as input into the previously described registration algorithm.

Once a frame is registered, the frame and the features identified in the frame may be saved electronically, or by any other known method. Any time a new still is presented to the system, a pattern-recognition algorithm determines whether a pattern in the still corresponds to a registered and saved pattern. If it does, any identified feature is recognized and identified in the new still, and the frame is updated.

The methods disclosed herein have another useful application during patient treatment such as during hair harvesting or implantation procedure, for example. Sometimes, after the image processor located and identified a particular follicular unit that is scheduled to be harvested, such follicular unit may be temporarily lost and disappear from the view, for example, due to the bleeding in the area, or due to the physician applying a Q-tip to the area and obscuring the follicular unit of interest. Without the present invention, in those circumstances, there will be a substantial delay in the procedure as the follicular unit of interest would have to be located and identified again. However, the ideas disclosed herein allow the system to proceed with the scheduled harvesting as the patient frame and the position of the follicular unit at issue is saved in the system and could be quickly recovered. Once the system has been positioned over the original registration pattern, a pattern-recognition algorithm recognizes that same pattern, and re-registers the frame. Because all other points are held with respect to patient frame coordinates, simply reregistering the frame causes all other previously known points to be instantly known again.

Figure 9A:
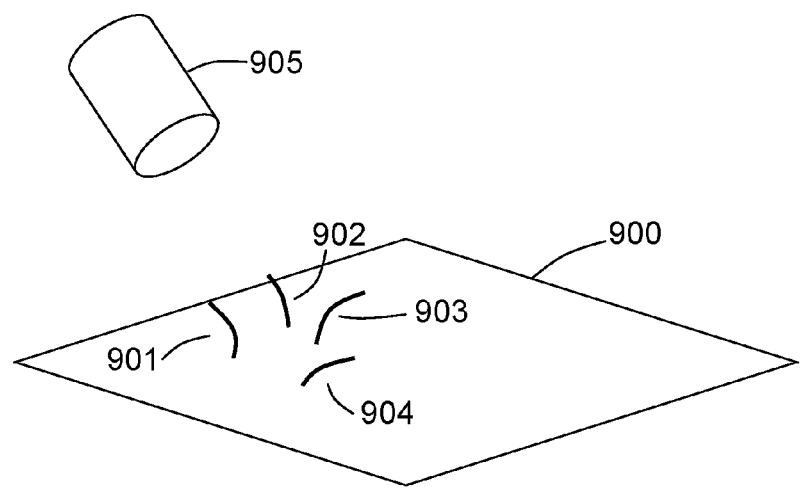
FIGS. 9A and 9B illustrate point-cloud tracking.
Figure 9B:
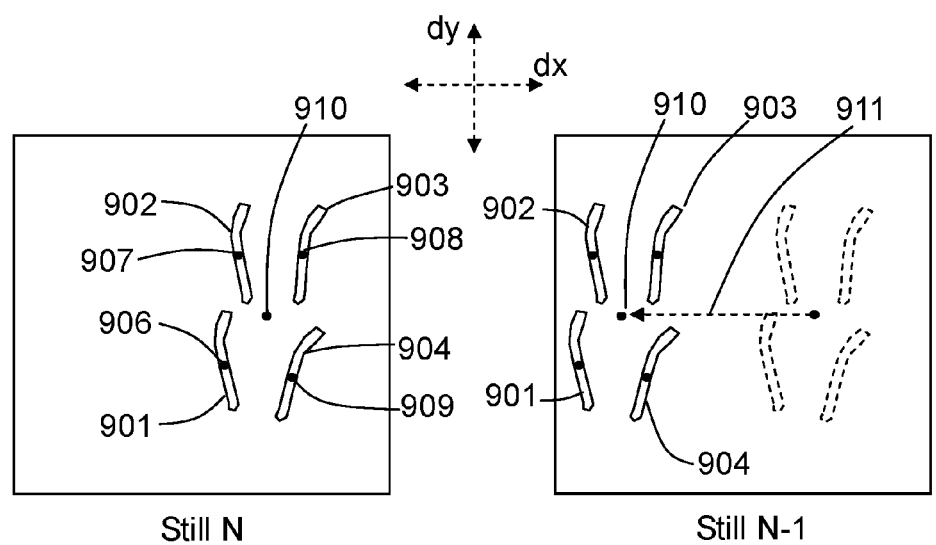

According to another aspect, a method of labelling or tracking hairs, follicular units, or other features of interest or objects from one still to the next involves calculating a motion vector. One method of tracking/labelling objects or features of interest, such as follicular units using a motion vector is illustrated in FIGS. 9A and 9B. FIG. 9A shows a body surface, such as a scalp 900, with four follicular units 901-904 which could be used as markers or fiducials. A camera 905 or any other image capture device records images of the scalp. Still N shows a first image including follicular units 901-904. Each follicular unit has a center-of-mass or "centroid," the collection of these follicular units is deemed a "point-cloud" and the point-cloud itself has a centroid. The system according to the present disclosure calculates the centroids 906-909 of each follicular unit comprising a point cloud. A centroid 910 of the point cloud is calculated based on the centroids 906-909 of the individual follicular units 901-904 that comprise the point cloud. The system includes an image processor that may be programmed and includes one or more components to perform background subtraction, segmentation and noise filtering of the image, for example, as described in the commonly owned Patent Publication WO 2008/024955.

Still N-1 shows a change in location of the follicular units 901-904 corresponding to a change in position of a patient, for example. The centroid 910 of the point cloud is calculated and compared to the location in still N. The system calculates a motion vector 911 of the point cloud corresponding to the change in position of the centroid 910 from still N to still N-1.

However, problems may arise when any of the follicular units 901-904 are obscured due to imaging noise, blood, or otherwise removed from stills. The system may confuse similarly located follicular units as the absent follicular unit or may generate a point cloud centroid that does not correspond to the centroid 910 corresponding to all four follicular units 901-904. One solution is to employ digital image stabilization to keep the same follicular units or other features or objects in subsequent stills.

Figure 10:
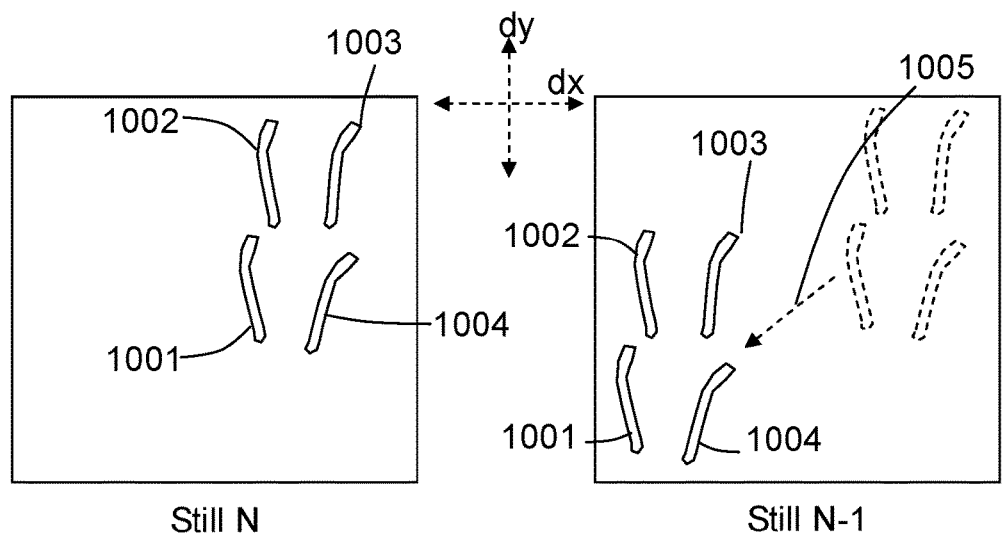
FIG. 10 illustrates motion vector calculation.

FIG. 10 illustrates a process of calculating a motion vector. Stills 0 and 1 contain four follicular units 1001-1004. The follicular units have changed location between still N and still N-1, which may correspond to patient movement, for example. The system compares stills 0 and 1 and uses a motion vector algorithm to calculate a motion vector 1005 of the patient's body surface.

While FIGS. 9-10 illustrate calculating motion vectors in two-dimensions where "dx" is the horizontal motion component and "dy" is the corresponding vertical motion component, the system may also calculate a three-dimensional motion vector. One method for calculating a 3D motion vector may include calculating an in-plane rotation theta. Another method includes using stereo geometry to acquire two images simultaneously from different angles. The relationship between the images is known with a high degree of precision. The stereo images may then be analyzed with the motion vector algorithm to obtain either a 2D or 3D motion vector. Once the system calculates a motion vector, the vector may be used to move an imaging device to keep an object or feature of interest in a subsequent still.

It is particularly important to maintain the same follicular units in subsequent stills during harvesting and implanting. An imaging device is used to generate stills of a body surface. The imaging device may be held by hand, by a robotic arm, or by any other mechanism. Of course, various image capture devices (or imaging devices) could be used with any of the embodiments of the systems and methods described herein. For example, the imaging device may be one or more cameras, such as any commercially available cameras. Or, the imaging device could be a video recording device (such as a camcorder). While it is preferred that the imaging device be a digital device, it is not necessary. It could be, for example, an analog TV camera that acquires an initial image which is then digitized into a digital image.

The physician examines the stills to determine which follicular units will be harvested and which locations will receive follicular units during implantation. During this process, it is helpful if body surface that is actually beneath the imaging device is the same as the still being examined by the physician. A physician can finish examining a still and immediately access the area in the still if the imaging device is kept in place with respect to the patient's body surface. This may be accomplished by continually feeding stills into the stabilizing system, analyzing motion vectors corresponding to patient movement, and moving the imaging device to correspond to the motion vectors. If the imaging device is supported by a robot arm, the robot arm location may be adjusted corresponding to the motion vectors.

Figure 11:
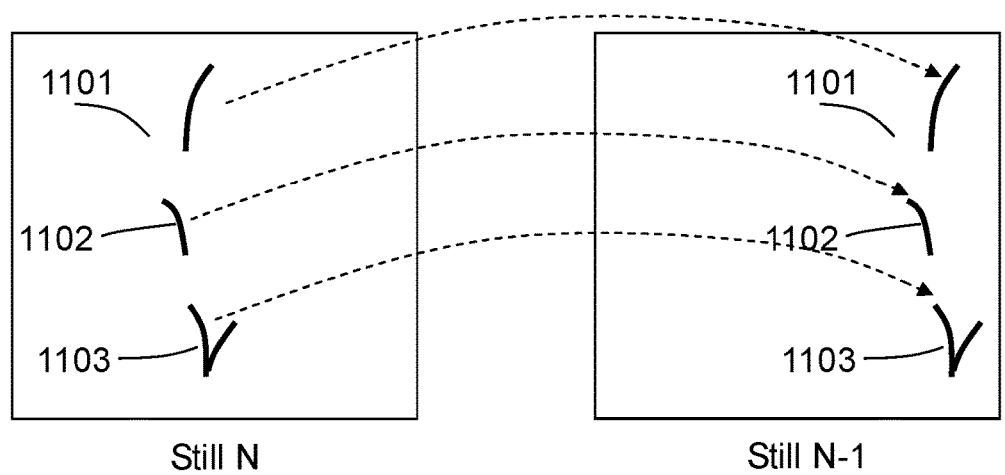
FIG. 11 illustrates follicular unit labelling.

One exemplary application is in improving the robustness of the follicular units tracking/labelling, for example, during automated hair harvesting procedure. During such a procedure, the system has to track the coordinates of individual follicular units in order to orient the harvesting tool and the mechanism operating the harvesting tool in preparation for hair harvesting. This is accomplished by assigning a unique label to each object in a still image, as shown in FIG. 11. In still N, follicular units 1101-1103 are recognized, their unique "signature" is identified, and they are labelled accordingly.

In preferred embodiments, the system analyzes characteristics of the follicular units (or other desired objects) to help identify the same follicular units in each subsequent still. Characteristics that may be used to identify follicular units, hairs, or other features include but are not limited to type, caliber, length, emergence angle, area, mass, color, and/or any combination of the above which would define the unique "signature" of such follicular unit or other feature used. Any other detectable characteristics or "tags" may be used as appropriate to the particular application. In still N-1, the same objects are located and labelled with the same labels. This may be done by searching in the nearby vicinity for the nearest object. This process may be made more robust and accurate by using both the determined "signature" of the follicular unit and a motion vector of the patient between still N and still N-1 to aid in locating the same objects in the two stills. Those skilled in the art will appreciate that while one follicular units or hair may be the object of interest for tracking, other follicular units in the neighbourhood may serve as the markers, and may be used to calculate the motion vector.

Figure 12:
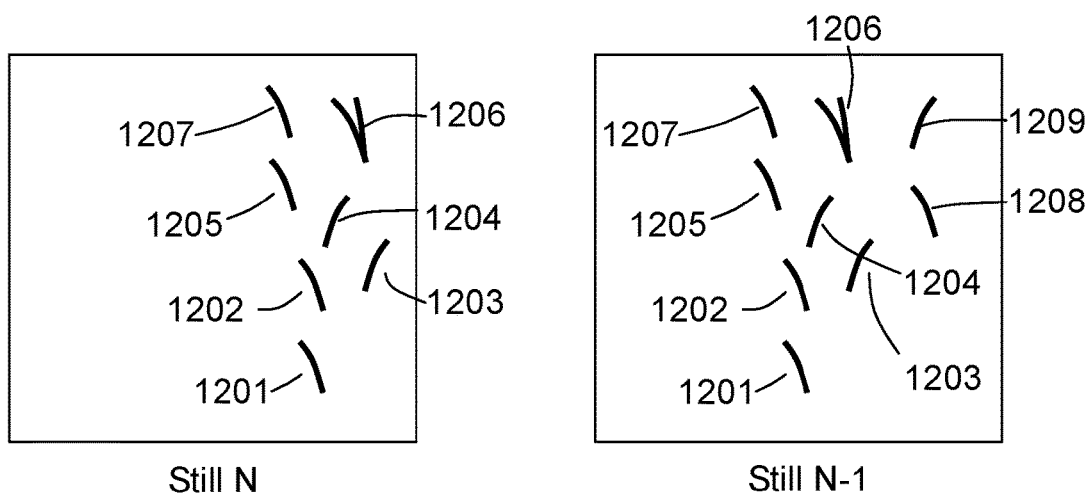
FIG. 12 also illustrates follicular unit labelling and associated issues.

In certain situations, the system may become confused, for example, if new follicular units or other features are introduced into a subsequent frame near a previously-identified follicular unit. FIG. 12 illustrates seven follicular units 1201-1207 in still N. Still N−1 contains nine follicular units, including 1201-1207 from still N, plus new follicular units 1208 and 1209. Follicular units 1208 and 1209 were outside the still's view area in still N, but if the patient moves relative to the image capture device, they appear in still N−1. If the system analyzes and identifies follicular units based only on vicinity to the location of follicular units in a previous still, it may confuse follicular units 1208 and 1209 with 1206 and 1203.

Figure 13A:
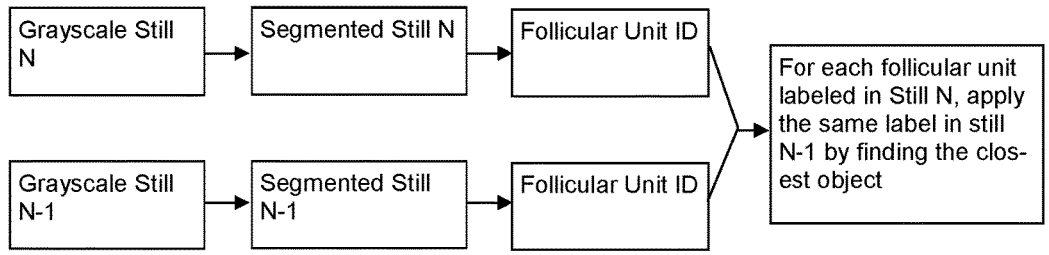
FIGS. 13A and 13B illustrate a follicular unit labelling/tracking process, and a follicular unit labelling/tracking process using a motion vector, respectively.
Figure 13B:
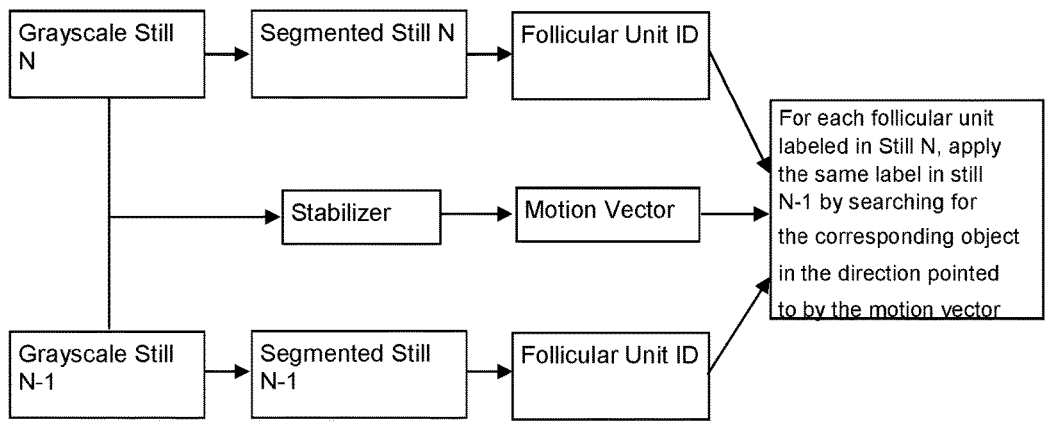

A preferred solution for providing a more robust identification of follicular units involves incorporating a digital image stabilizer in the tracking loop and using it in combination with the unique signature information of the relevant follicular unit, as shown in FIGS. 13A and 13B. FIG. 13A depicts a method of labelling follicular units or other features extracted from grayscale stills, and identifying follicular units in a still N−1 by finding the closest object to the follicular unit previously identified in still N. In this process, grayscale stills may be converted to the segmented stills (for example, binary stills) consisting purely of foreground objects (for example, follicular units). Background components are removed from the still using image processing techniques well-known to those skilled in the art.

FIG. 13B illustrates the same process, but improved with image stabilization methodology and signature information. The system analyzes grayscale stills N and N−1 and determines follicular unit ID (including its signature information). The stills are compared to calculate a motion vector, the stills are segmented, and the follicular unit signature and the motion vector is applied to the frame N−1 to search for an object corresponding to a follicular unit of the first frame by searching in a direction of the motion vector. Using this extra information about the motion-induced "flow" of objects in the image, one can discard completely follicular units 1208 and 1209 shown in FIG. 12 because the motion-induced flow is towards the lower-left corner of the image and the signature of the follicular unit 1209 does not correspond to the signature of the follicular unit 1206. This is because, follicular unit 1206 is an F2 containing two hair follicles while follicular unit 1209 is a single-hair F1.

Figure 14:
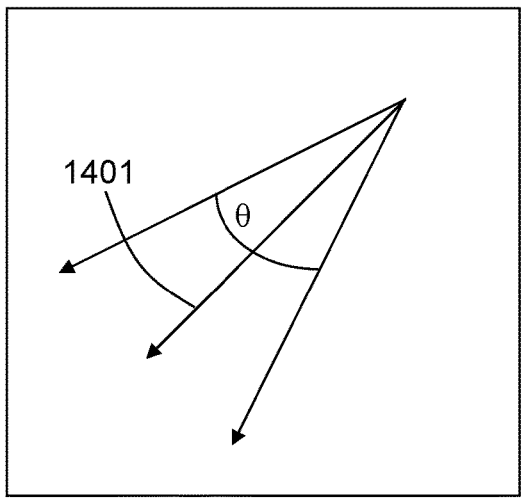
FIG. 14 illustrates defining a search region.

By applying the image stabilization analysis, the chance of mis-labelling is substantially reduced, because the system searches in the direction of the movement vector rather than in the vicinity of the follicular unit in the first still. FIG. 14 illustrates an example of defining a search field based on a general direction pointed to by the measured motion vector. Motion vector 1401 may be calculated as disclosed above. Some leeway may be desired in setting the tracking parameters, which is accomplished, for example, by specifying an angle, θ, that is used to define a search area on either side of the movement vector where the system searches for the object.

Figure 15:
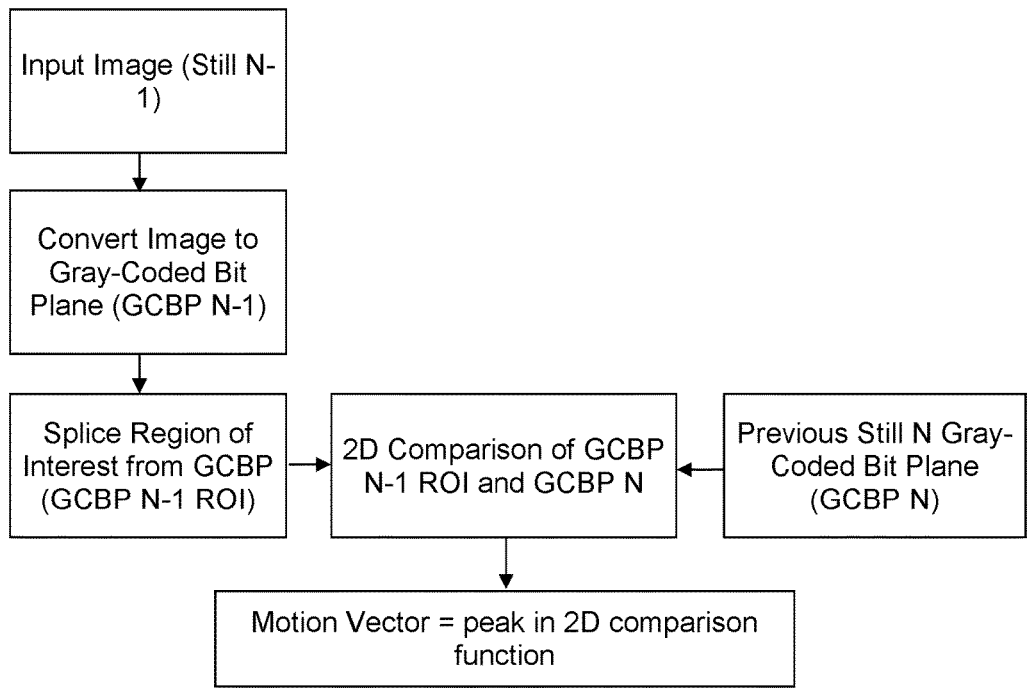
FIG. 15 illustrates one exemplary image-stabilization process.
Figure 16:
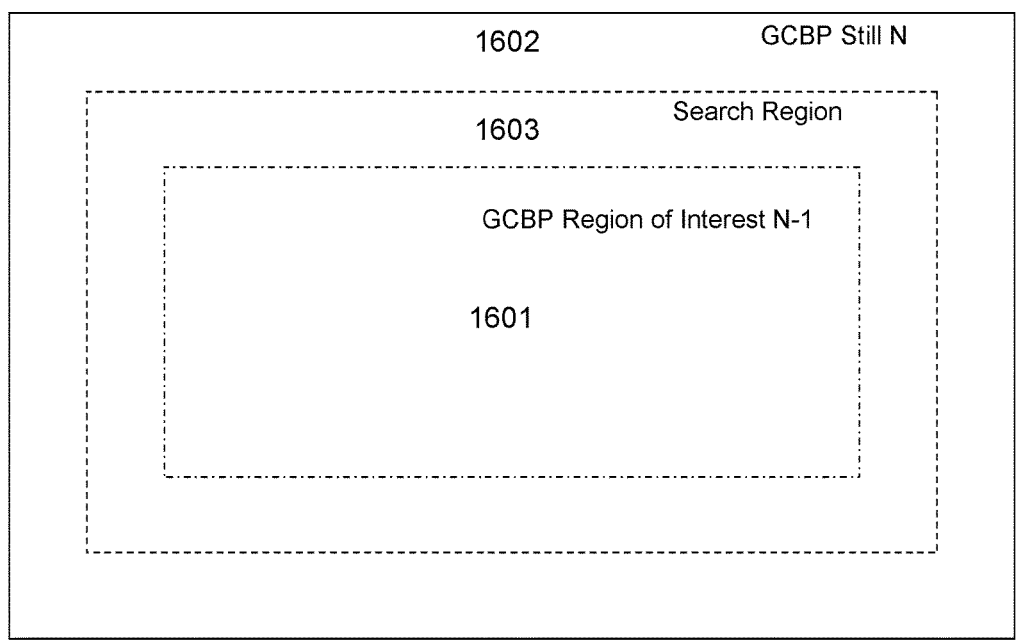
FIG. 16 illustrates an image comparison.

Many digital image stabilization algorithms may work with the method described herein to result in a robust system for identifying features or follicular units. One such algorithm which is incorporated herein by reference in its entirety is an approach using a gray-coded bit-plane (GCBP) as described in S. Ko, S. Lee, S. Jeon, and E. Kang. *Fast digital image stabilizer based on gray-coded bit-plane matching*. IEEE Transactions on Consumer Electronics, vol. 45, no. 3, pp. 598-603, August 1999. Implementation of the gray-coded bit-plane approach is illustrated in FIG. 15. First, an input image is received from an imaging device. The image is translated into a gray-coded bit-plane. In some embodiments, a region of interest 1601 may be spliced from the gray-coded bit-plane 1602 to reduce the search area and strain on computing components, as shown in FIG. 16. A search region 1603 that is smaller than the GCBP still but larger than the region of interest 1601 may also be defined. The gray-coded bit plane of the region of interest is compared with the gray-coded bit plane of a previous image.

In contrast to the point-cloud approach of calculating motion vectors, where the calculations to deduce overall movement of the cloud takes place in "object space" (requires knowledge of the centroids of the follicular units or other markers), the GCBP image stabilization approaches mentioned above operate purely on the pixel intensity data, without any a priori knowledge of where particular features, for example, follicular units are located, or even if there are follicular units in the scene. This has the strong benefit of providing a completely independent measure of motion, which is useful in tracking because extraction of follicular unit coordinates can be a noisy measure due to the dynamic nature of the scene being imaged.

There are numerous other digital image stabilization algorithms that may be used instead of the gray-coded bit plane. Some of the examples of such stabilization algorithms include but are not limited to the "optical flow" technique described in Jean-Yves Bouquet. *Pyramidal Implementation of the Lucas Kanade Feature Tracker*. Intel Corporation; a "block search" technique, as described in Vella F et al. *"Robust digital image stabilization algorithm using block motion vector."* Consumer Electronics, ICCE, p. 234-235, 2002 or in Sun Yi et al. *"Real-time digital image stabilization algorithm on PC."* Electronic Imaging and Multimedia Technology III, SPIE Vol. 4925, p. 510-513.

"Optical flow" estimation algorithms compute a field of vectors that together approximate the perceived motion of objects within an image, or series of images (as in video). A vector is calculated from a certain point within the image or image(s) that represents the localized motion nearby that point. In the Bouguet article, cited above, the optical flow calculations are estimated using a pyramidal and hierarchical search method. An initial guess of the localized motion is estimated from a low resolution version of the image(s), which is successively refined as the algorithm traverses "up the pyramid" utilizing higher-resolution versions of the image(s).

"Block search" methods borrow techniques commonly employed in video compression standards like MPEG. As described in Vella (cited above), the key change between block search employed in video compression and that used in digital image stabilization is that the image(s) are first split into foreground and background components. Foreground and background are in turn split into sections where each section is assigned a separate weight. A motion vector is computed for each section and given its weight. The weighted motion vectors are combined to form a single vector for background and foreground. A heuristic is then used to choose which of the two motion vectors to use for the stabilization.

Finally, the method described herein for further improvement of the robustness of the labelling/tracking mechanism may employ both computing a motion vector based on one or more objects or markers in the image and in addition also computing a motion vector from the image itself as in the above-mentioned articles, so that the total calculation is based on both motions vectors.

Figure 17:
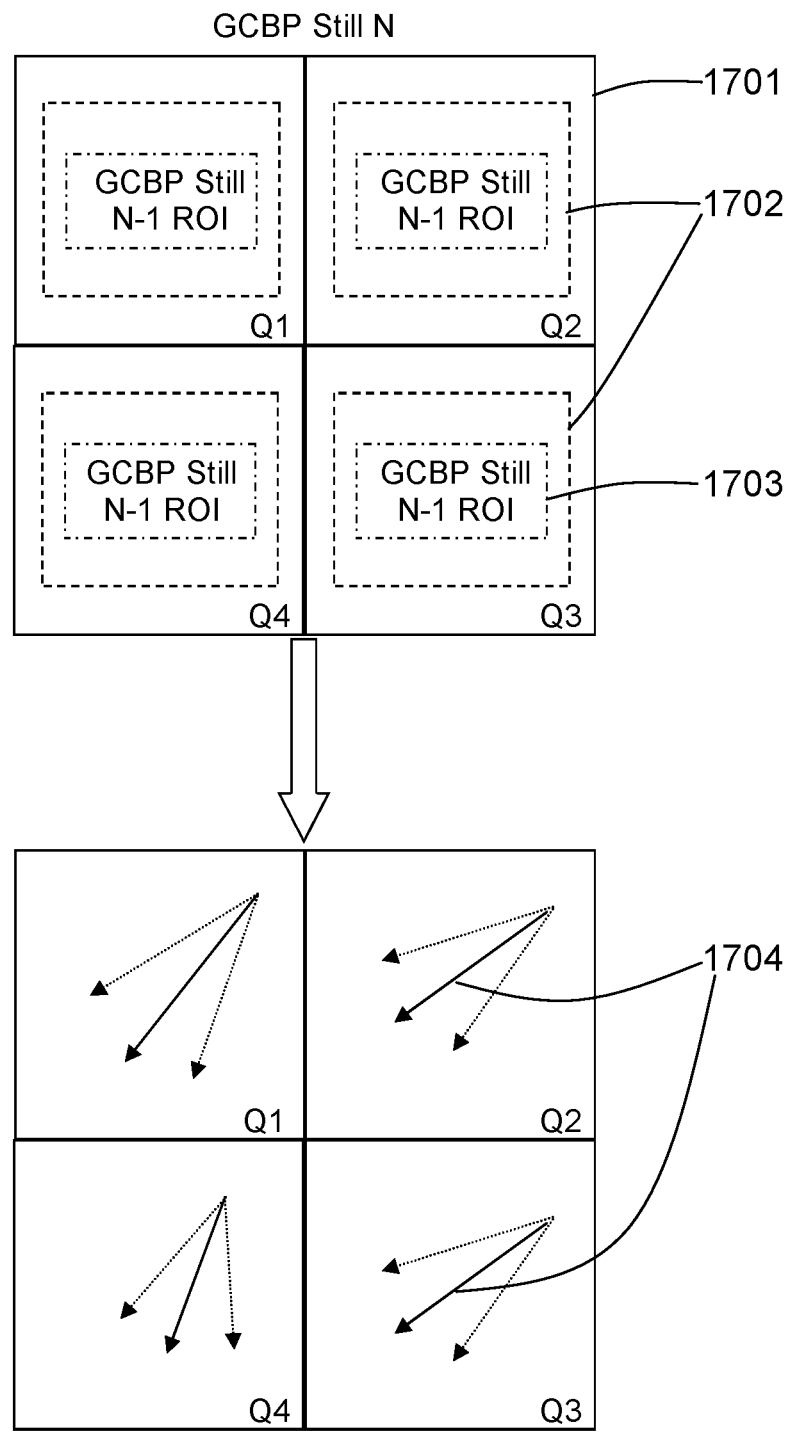
FIG. 17 illustrates an image stabilization with multiple vectors calculated.

Further, in one implementation of this system, the stills may be split into multiple images to generate multiple vectors, as illustrated in FIG. 17. Still N is divided, for example, into four sections, Q1-Q4. Each section 1701 corresponds to at least one different feature or follicular unit. A subsequent still N-1 is also divided into corresponding sections and may be further spliced into corresponding search areas 1702 and regions of interest 1703. The sub-sections are compared and a motion vector may be obtained for each sub-section. The resulting motion vectors may indicate rotational movement of the patient with the increased accuracy.

In any of the methods for calculating a motion vector, a still may be either a reference still, or a changeable still. For example, a reference still image may be taken of a region of skin on the patient's body. Then, each subsequent still image may be compared to the reference still image to determine a motion vector. The motion vector may be used to direct an imaging device to move in the direction of the vector so that the image in the imaging device is the same as the reference still. Alternatively, the system may compare a second still to a first still, calculate a movement vector, and move an imaging device according to the movement vector. A subsequent third still may then be compared to the second still, and the process repeated. In this case, each subsequent still is compared to the previous still, rather than to a reference still.

Although the motion vector may be used to move an imaging device, it may also be used as tracking data or any other purpose. For example, the system may record patient movement by recording movement vectors for a predetermined time period or a predetermined number of stills. The system may also be programmed to move an imaging device only when a certain amount of movement, or a certain movement vector magnitude has been reached. For example, the system may be programmed to make sure a predetermined follicular unit, location, or point is always within the field of view of the imaging device, or within a predetermined area in the field of view of the imaging device.

Another exemplary application of the image stabilization technique involves stabilizing the images during the automated hair harvesting process. During such automated hair harvesting, all follicular units in a given image may be sorted based on a scoring system, so that a particular follicular unit to be harvested next can be selected. Typically, there will be a pause during the procedure when the operator looks, for example, at the screen of the computer or other appropriate display to confirm that the image processor correctly chosen the best follicular unit to harvest according to the selected criteria. During this time when an operator is inspecting a static still image of the body surface, a patient may move, therefore, it is desirable to keep the video stabilized during this period of time.

Importantly, once the user confirms the choice (or even selects a different one), the system needs to ensure that the selected follicular unit is still in the live still. This is achieved through employing the results of digital image stabilization according to the present disclosure. In some embodiments, the 3D motion vector output from the stereo image stabilizer is negated and passed, for the example, to the robotic arm (in the robotically operated systems). This has an effect of negating the patient motion, or moving one or more cameras that could be mounted on the robotic arm, such that the same field of view will be imaged in subsequent image acquisitions.

Yet another exemplary application of the image stabilization technique involves using the output of the stabilizer to guide the robotic system during hair implantation. Exemplary robotic systems and methods for hair transplantation and treatment planning are described in the commonly owned U.S. Publication 2007/0078466 and U.S. patent application Ser. No. 12/133,159, which are incorporated herein by reference in their entirety. When any of the above-mentioned systems is used, follicular units may be implanted in the locations prescribed by the selected treatment plan.

Typically, the hair recipient areas are sparse in terms of the number of follicular units that an imaging system can reliably track. That is why there is a need to keep track of the motion of the robot or patient motion through some other means aside from tracking follicular units. This can be achieved by tracking the motion of the body surface (e.g. scalp) via the image stabilizer. The treatment plan can be registered with the recipient area using external fiducials. This registration established a coordinate frame of reference which has to be updated as the robot and patient move during the treatment. The coordinate frame of reference (coordinate system) may be updated by the visual system by identifying the locations of the fiducials. However, even if the fiducials cannot be seen sometimes, as previously explained, one can continue to update the coordinate system in a delta fashion by adding the measured motion vector on a still by still basis.

Figure 18:
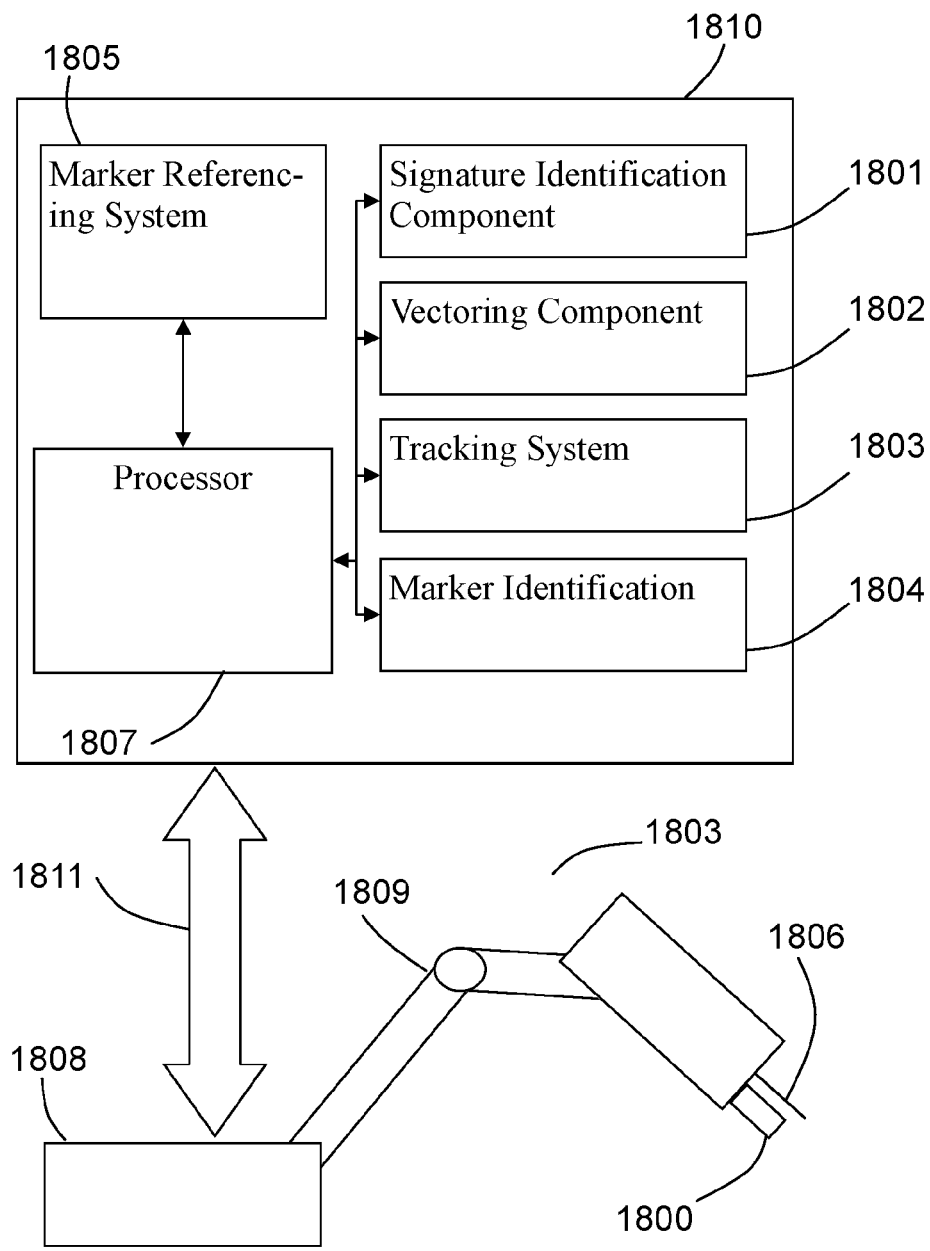
FIG. 18 illustrates an exemplary system that tracks objects.

An exemplary system for tracking a follicular unit, a marker, or another object is illustrated in FIG. 18. In some embodiments, the system may include an imaging device 1800, a signature identification component 1801, a vectoring component 1802, and a tracking system 1803. The imaging device 1800 may include a camera such as a video camera. Alternatively, any other device capable of capturing an image may be used. Preferably, the imaging device is a digital imaging device. In other embodiments, an imaging device may be provided separately and not included in the system. In those embodiments, an interface may be provided that allows various other components or modules of the system, such as signature identification component, to interact with the separate imaging device.

The imaging device 1800 interacts with the signature identification component 1801 to identify a follicular unit, a marker, or another object. The signature identification component 1801 may be a software program with code stored on a portable disk, a hard disk, or other memory. The code may interact with a computer system 1810 including, for example, a processor 1807 to identify distinguishing characteristics of a follicular unit, a marker, or another object. Alternatively, the signature identification component 1801 may be embodied in a hardware platform, for example, Field-Programmable Gate Array ("FPGA") or Application-Specific Integrated Circuit ("ASIC"), and interact with a computer system 1810 or a processor 1807. The computer system 1810 or processor 1807 interacts with the imaging device 1800 via an interface 1811. The interface may include hardware ports, cables, leads, and other data transmission means, or it may comprise a computer program.

As discussed above, type, caliber, length, emergence angle, area, color, and/or any combination of the above may be used to define the unique "signature" of a follicular unit or other feature or object. Any other detectable characteristics or "tags" may be used as appropriate to the particular application. The signature identification program 1801 analyzes the image from the imaging device, identifies characteristics of a follicular unit or other feature, and electronically tags the follicular unit or other feature with an electronic signature.

When two or more stills are available, in certain embodiments according to the methods described herein the vectoring component 1802 may be used to assist the tracking system in tracking a follicular unit or other feature. The vectoring component 1802 may be a software program or hardware that interacts with a computer system 1810 including a processor 1807 to analyze movement of the follicular unit. The vectoring component 1802 receives location information for a known feature. The known feature may have been identified by the signature identification unit 1801, for example. The location information is based on the location of the known feature in the stills. The vectoring component 1802 uses the location information to calculate a vector of the known feature.

Information from the vectoring component 1802 may be used to track a follicular unit or other feature using the tracking system 1803. The tracking system 1803 may include a robotic base 1808 and arm 1809, a movement adjustment mechanism in the imaging device, code for presenting an image or a portion of an image on a screen, or any other mechanism for tracking an object between multiple stills. If the tracking unit comprises a robot arm 1809, the imaging device 1800 and a harvesting or an implantation tool 1806 may be located at the end of the robot arm 1809. The vector from the vectoring component 1802 may be used to move the tracking system 1803 in the movement direction of the stills to keep the target follicular unit or other feature in the live still.

In one embodiment, a marker identification component 1804 is used to identify markers in stills. The marker identification component may be, for example, a software program, or it may be embodied in hardware as mentioned above in reference to other components, that interacts with the computer system 1810 including the processor 1807. This marker identification component may also be a part of the signature identification component 1801.

In another embodiment, a system for tracking a feature of interest comprises an interface, such as interface 1811, adapted to receive a plurality of images from an imaging device (which may not be included in a system itself), a signature identification component, such as 1801, and a marker referencing system 1805. The marker referencing system 1805 receives information corresponding to a marker, follicular unit, or other feature identified by the signature identification component 1801 in a first image and defines a frame of reference corresponding to the marker. It then determines whether the marker is in a second image, and adjusts the frame of reference corresponding to a change in position of the marker between images. The system may include data stored in memory, including a portable disk, a hard disk, flash memory, or any other memory medium. It may also include a processor independent of processor 1807, or it may use the same processor 1807.

The above components, including the signature identification component, the vectoring component, the tracking system, the marker identification system, and the marker referencing system may be part of one software or hardware component, or may comprise multiple software and hardware programs and modules. Each module may be separable from any other module, or all the modules may be integral in one device or chip. In various embodiments and methods described herein, some of these components may be optional.

While one embodiment may include analysis of a body surface, the above system and method may track any object and automatically update a frame or calculate a motion vector based on any object or set of objects. Objects that may be tracked include airborne objects, objects moving along a surface, objects moving on the earth, or any other objects that need to be identified or tracked.

The various embodiments described above are provided by way of illustration only and should not be construed to limit the claimed invention. Those skilled in the art will readily recognize various modifications and changes that may be made to the claimed invention without following the example embodiments and applications illustrated and described herein, and without departing from the true spirit and scope of the claimed invention, which is set forth in the following claims.

What is claimed is:

1. A method for labeling hair for use in hair transplantation procedure, the method comprising:
   obtaining an image of a region of interest;
   identifying follicular units in the region of interest, including their location and orientation;
   classifying the follicular units in the region of interest into follicular unit classes based on a number of hairs in the respective follicular units, wherein the follicular unit classes represent the number of hairs in each respective follicular unit;
   labeling and recording the follicular units according to their location and classification; and
   using the follicular units labeling for planning hair transplantation, or real-time harvesting, including determining which follicular units to harvest from the region of interest based on the follicular unit classes of the follicular units in the region of interest.

2. The method of claim 1, wherein identifying follicular units comprises identifying one or more characteristics from a following list: color, length, type, shape, and emergence angle.

3. The method of claim 1, further comprising counting the follicular units in the region of interest.

4. The method of claim 1, further comprising determining how many follicular units per $cm^2$ to extract from the region of interest based on the classification and a desired density in an implanting area.

5. The method of claim 1, further comprising analyzing the follicular units to determine a follicular unit density, baldness pattern, or other criteria for implanting follicular units.

6. The method of claim 1, comprising obtaining the image with an image acquisition device and transmitting the obtained image to an image processor.

7. The method of claim 6, wherein the image processor generates a hair implantation plan based on information in the image, and wherein the image processor is operatively connected to a robotic hair transplantation system that is configured and programmed to implement the plan.

8. The method of claim 1, comprising identifying one or more marker in the image, and wherein identifying the one or more marker comprises analyzing at least one of a length, an area, a shape, a type, or a color of the at least one marker.

9. The method of claim 8, wherein the one or more marker is a follicular unit and identifying the at least one marker further comprises analyzing at least one of the emergence angle of the follicular unit from the body surface and a caliber of the hair.

10. The method of claim 1, further comprising utilizing a clustering algorithm to locate any bald spots in the image, and generating implantation sites located within the bald spots.

11. A system for labeling hair, the system comprising:
an interface configured to receive image data corresponding to a region of interest containing follicular units;
an image processor comprising one or more modules for executing operations on the image data, the one or more modules including instructions for:
identifying follicular units in the region of interest, including their location and orientation;
classifying the follicular units in the region of interest into follicular unit classes based on a number of hairs in the respective follicular units, wherein the follicular unit classes represent the number of hairs in each respective follicular unit;
labeling and recording the follicular units according to their location and classification; and
using the labeled follicular units to plan hair transplantation, or real time harvesting, including determining which follicular units to harvest from the region of interest based on the follicular unit classes of the follicular units in the region of interest.

12. The system of claim 11, further comprising an image acquisition device, the image acquisition device providing image of a video feed, photographs, or other representation of the region of interest.

13. The system of claim 11, wherein the image processor is operatively connected to a robotic hair transplantation system configured to implement the planned hair transplantation or the real-time harvesting.

14. The system of claim 11, wherein the one or more modules includes instructions for determining a follicular unit density, baldness pattern, or other criteria for implanting follicular units.

15. The system of claim 11, wherein the follicular units are sorted according to selected criteria, and the image processor is configured to select a particular follicular unit to be harvested based on the selected criteria.

16. The system of claim 11, wherein the system comprises an implantation planning system and the region of interest comprises a recipient area, and wherein the one or more modules includes instructions for locating a bald spot within the recipient area using a clustering algorithm and generating implantation sites within the bald spot.

17. The system of claim 11, the system further comprising:
a marker referencing system configured to detect at least one marker, determine a frame of reference corresponding to the at least one marker, and adjust the frame of reference corresponding to a change in position of the at least one marker.

18. The system of claim 17, wherein the image processor is further configured to define a frame of reference based on a pixel intensity data, without any a priori knowledge of the follicular unit locations.

19. The system of claim 11, wherein the system further comprises image stabilization algorithms configured to substantially reduce a chance of mis-labeling the follicular units.

20. A system for labeling hair, the system comprising:
an interface configured to receive image data corresponding to a region of interest containing follicular units;
an image processor comprising one or more modules for executing operations on the image data, the one or more modules including instructions for:
identifying follicular units in the region of interest, including their location and orientation;
classifying the follicular units in the region of interest based on a number of hairs in the respective follicular units;
labeling and recording the follicular units according to their location and classification; and
using the labeled follicular units to plan hair transplantation, or real time harvesting and/or implantation;
the system further comprising:
a marker referencing system configured to detect at least one marker, determine a frame of reference corresponding to the at least one marker, and adjust the frame of reference corresponding to a change in position of the at least one marker;
wherein the image processor is further configured to define a frame of reference based on a pixel intensity data, without any a priori knowledge of the follicular unit locations.

* * * * *